United States Patent
Ko et al.

(10) Patent No.: US 9,029,608 B2
(45) Date of Patent: May 12, 2015

(54) APPARATUS FOR COPRODUCTING ISO TYPE REACTION PRODUCTS AND ALCOHOLS FROM OLEFINS, AND METHOD FOR COPRODUCTING THEM USING THE APPARATUS

(71) Applicant: LG Chem, Ltd., Seoul (KR)

(72) Inventors: Dong-Hyun Ko, Daejeon (KR); Moo-Ho Hong, Daejeon (KR); Sung-Shik Eom, Daejeon (KR); Yong-Jin Choe, Daejeon (KR); O-Hak Kwon, Daejeon (KR); Dae-Chul Kim, Daejeon (KR); Jae-Hui Choi, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 14/275,723

(22) Filed: May 12, 2014

(65) Prior Publication Data

US 2014/0249333 A1    Sep. 4, 2014

Related U.S. Application Data

(63) Continuation of application No. 13/809,565, filed as application No. PCT/KR2011/005046 on Jul. 11, 2011, now Pat. No. 8,791,304.

(30) Foreign Application Priority Data

Jul. 14, 2010  (KR) ................. 10-2010-0067688
Apr. 8, 2011   (KR) ................. 10-2011-0032435

(51) Int. Cl.

| | |
|---|---|
| *C07C 45/50* | (2006.01) |
| *C07C 29/16* | (2006.01) |
| *C07C 45/82* | (2006.01) |
| *B01J 8/00* | (2006.01) |
| *C07C 29/141* | (2006.01) |
| *C07C 29/17* | (2006.01) |
| *C07C 45/74* | (2006.01) |

(52) U.S. Cl.
CPC ............. *C07C 45/50* (2013.01); *C07C 45/82* (2013.01); *C07C 29/16* (2013.01); *B01J 8/00* (2013.01); *C07C 29/141* (2013.01); *C07C 29/175* (2013.01); *C07C 45/74* (2013.01)

(58) Field of Classification Search
CPC ........................................................ C07C 45/50
USPC .................................... 568/451, 882, 883
See application file for complete search history.

(56) References Cited

U.S. PATENT DOCUMENTS

| 4,684,750 A | 8/1987 | Kessen et al. |
|---|---|---|
| 2002/0028974 A1 | 3/2002 | Scholz et al. |

FOREIGN PATENT DOCUMENTS

| JP | S38-001364 BA | 2/1938 |
|---|---|---|
| JP | 06-122638 | 5/1994 |
| JP | 2003-171338 | 6/2003 |
| JP | 2006-1893 | 1/2006 |
| JP | 2008-147129 | 6/2008 |
| KR | 10-2006-0110868 | 10/2006 |
| KR | 10-2008-0104710 | 12/2008 |
| KR | 10-2008-0105004 | 12/2008 |
| KR | 10-2010-0058713 | 6/2010 |
| KR | 10-2010-0084311 | 7/2010 |
| KR | 10-2011-0038324 | 4/2011 |
| WO | 2010/082793 | 7/2010 |

*Primary Examiner* — Sikarl Witherspoon
(74) *Attorney, Agent, or Firm* — McKenna Long & Aldridge LLP

(57) ABSTRACT

The present invention relates to an apparatus for coproducting iso-type reaction product and alcohol from olefin, and a method for coproducting using the apparatus, in which the hydroformylation reactor provides a sufficient reaction area due to the broad contact surface area between the olefin and the synthesis gases that are the raw materials by a distributor plate installed in the reactor, and the raw materials can be sufficiently mixed with the reaction mixture due to the circulation of the reaction mixture so that the efficiency of the production of the aldehyde is excellent; and also the hydrogenation reactor suppresses the side reaction so that the efficiency for producing aldehyde and alcohol are all increased, and also iso-type reaction product and alcohol can be efficiently co-produced.

8 Claims, 1 Drawing Sheet

APPARATUS FOR COPRODUCTING ISO TYPE REACTION PRODUCTS AND ALCOHOLS FROM OLEFINS, AND METHOD FOR COPRODUCTING THEM USING THE APPARATUS

This application is a Continuation of U.S. patent application Ser. No. 13/809,565, filed Jun. 20, 2013, which is a National Stage entry of International Application No. PCT/KR2011/005046 filed on Jul. 11, 2011, and claims priority of U.S. Korean Application Nos. 10-2010-0067688 filed Jul. 14, 2010 and 10-2011-0032435 filed Apr. 8, 2011, all of which are incorporated by reference in their entirety herein.

TECHNICAL FIELD

The present invention relates to an apparatus for coproducting iso-type reaction products and alcohols from olefins, and a method for coproducting them using the apparatus, and more specifically, to an apparatus for coproducting iso-type reaction products and alcohols from olefins, and a method for coproducting them using the apparatus, in which the apparatus comprises a hydroformylation reactor; a first main distillation column; a hydrogenation reactor; a fore distillation column; a second main distillation column; a post distillation column; and a pipe for connecting them; in which any one of the first main distillation column and the second main distillation column is operated during the reaction.

BACKGROUND ART

A hydroformylation reaction that is generally well known as OXO reaction is the process for producing a linear (normal) and branch-(iso) aldehyde, in which the olefin is added with one carbon atoms by react all kinds of olefins and synthesis gases ($CO/H_2$) in the presence of a metal catalyst and a ligand.

All kinds of aldehydes that are synthesized by OXO reaction are modified into acids and aldehydes that are aldehyde derivatives, and alcohols through an oxidation or a reduction reaction. Also, they can be modified into various acids, aldehydes and alcohols comprising long alkyl group through the oxidation or reduction reaction after a condensation reaction, such as aldol, and the like. Those aldehydes, alcohols, and acids are being used as a raw material for solvents, additives, and plasticizers.

The representative example of hydroformylation is to produce octanol (2-ethylhexanol) from propylene using a rhodium based catalyst. Octanol is mainly used as a raw material for PVC plasticizer, such as DOP (dioctyl phathalate), and also as an intermediate raw material for synthetic lubricants, surfactants, and the like.

Propylene is injected with a catalyst into OXO reactor using synthesis gases ($CO/H_2$) to produce normal-butylaldehydes and iso-butylaldehydes. The produced aldehyde mixture is transferred to a separator along with catalyst mixture to separate into hydrocarbon and catalyst mixture, and then the catalyst mixture is circulated into the reactor and the hydrocarbon is transferred to a stripper. The hydrocarbon in the stripper is stripped by fresh synthesis gases to recover non-reacted propylene and synthesis gases into OXO reactor and transfer butylaldehydes to a fractionation column thereby separating normal-butylaldehydes and iso-butylaldehydes, respectively. Normal-butylaldehydes of the fractionation column bottom is transferred to a hydrotreated reactor, and then adding hydrogen products n-butanol. Alternatively, normal-butylaldehydes are introduced into an aldol condensation reactor to produce 2-ethylhexanal through a condensation and dehydration reaction, and then transferred to the hydrotreated reactor to be octanol (2-ethylhexanol) by adding hydrogen.

The hydroformylation reaction may be performed in a continuous, semi-continuous or batch type, and a typical hydroformylation reaction is a gas or liquid circulation system. It is important for the hydroformylation reaction to increase the reaction efficiency by smoothly contacting the starting materials that are composed of a liquid phase and gas phase. For this reason, conventionally the continuous stirred tank reactor (CSTR) that stirs for evenly contacting the liquid phase and the gas phase inside the reactor was mainly used. In addition, U.S. Pat. No. 5,763,678 discloses the hydroformylation method, in which the circulation is used instead of the stirring by applying the reactor that is a type of loop. However, those methods have a limit to the improvement of the hydroformylation reaction efficiency and also single reactor cannot produce the satisfactory aldehyde product, so that the residence time of the reaction is made to be longer, or more than two reactors are connected in series thereby producing the product that has a required level.

In addition, the hydrogenation process of aldehydes generally uses the reactor, in which nickel-based or copper-based solid hydrogenation catalyst is filled inside the reactor. There are two ways for performing the reaction, such that the starting aldehydes are evaporated to perform the reaction in a vapor phase, or the starting aldehydes are introduced into the reactor as a liquid to perform the reaction in a liquid phase.

However, there is a problem that the selectivity of the reaction is reduced by generating an undesirable side reaction, such as esterification, acetal formation, etherification, and the like in the above reaction, even though the above catalysts types, the vapor phase, or the liquid phase are applied.

DISCLOSURE OF INVENTION

Technical Problem

In order to solve the conventional technical problems as mentioned above, an object of the present invention provides an apparatus for coproducting iso-type reaction products and alcohols from olefins, and a method for coproducting them using the apparatus.

Solution to Problem

The present invention is to provide an apparatus for co-production of iso-type reaction product and alcohol form olefin as one mean for solving the above objects, in which the apparatus includes a hydroformylation reactor; a first main distillation column; a hydrogenation reactor; a fore distillation column; a second main distillation column; a post distillation column; and a pipe for connecting them, and only one of the first main distillation column and the second main distillation column is operated.

As another mean for solving the above objects as mentioned above, the present invention provides a method for co-production of iso-type reaction product and alcohol from olefin, comprising: hydroformylating for obtaining aldehyde by reacting micro-bubbles and the catalyst mixed solution while converting a spraying flow of olefin and the synthesis gases after forming the micro-bubbles of synthesis gases and olefin by spraying olefin and a synthesis gases ($CO/H_2$) in the catalyst mixed solution by using the second main distillation column from the above apparatus;

discharging iso-type alcohol from the second main distillation column through the fore distillation column by using the hydrogenation reaction product obtained by adding hydrogen to the normal-aldehyde and iso-aldehyde that are the hydroformylation products; and discharging normal-type alcohol from the post distillation column.

As another mean for solving the above objects, the present invention provides a method for co-production of iso-type reaction product and alcohol from olefin, comprising:

hydroformylating for obtaining aldehyde by reacting the micro-bubbles and the catalyst mixed solution while converting a spraying flow of olefin and the synthesis gases after forming the micro-bubbles of synthesis gases and olefin by spraying olefin and synthesis gases ($CO/H_2$) in the catalyst mixed solution by using the first main distillation column from the above apparatus;

discharging iso-type aldehyde among the hydroformylation reaction product that is the product of the hydroformylation from the first main distillation column; and separating normal-type alcohol from the post column through the fore distillation column by using the hydrogenation reaction product that is the product obtained by adding hydrogen to the normal-component that is the residue of the main distillation column.

As another mean for solving the above objects as mentioned above, the present invention provides a method for co-production of iso-type reaction product and alcohol from olefin, comprising: hydroformylating for obtaining aldehyde by reacting the micro-bubbles and the catalyst mixed solution while converting the spraying flow of the olefin and the synthesis gases after forming the micro-bubbles of synthesis gases and olefin by spraying olefin and the synthesis gases ($CO/H_2$) in the catalyst mixed solution by further using an aldol condensation kettle to the first main distillation column among the above apparatus; discharging iso-type aldehyde among the hydroformylation reaction product that is the product obtained by the hydroformylation from the first main distillation column; producing aldehyde having an increased carbon atoms by the aldol condensation of the normal-component that is a residue of the main distillation column; and separating alcohol component having an increased carbon atoms from the post distillation column through the fore distillation column by using the hydrogenation reaction product obtained by adding hydrogen to the aldehyde having an increased carbon atoms that is the product obtained from the aldol condensation.

Hereinafter, an apparatus for coproducing iso-type reaction products and alcohols from olefins according to an example of the present invention will be described in detail with reference to accompanying drawings.

Firstly, the term, iso-type reaction product, used for the present invention relates to a meaning including all of alcohol and iso-type aldehyde, and for example includes iso-butylaldehyde, iso-butanol, and the like.

In addition, the term, alcohol, used for the present invention is alcohol not iso-type, and for example, includes normal-type normal-butanol, 2-ethylhexanol, and the like.

FIG. 1a roughly shows an apparatus for co-production of iso-type aldehyde and normal-type alcohol from olefin according to an embodiment of the present invention. The figure showing all of the pipes are not shown due to the expression.

The apparatus for producing iso-type aldehyde and normal-type alcohol from olefin according to an embodiment of the present invention is used for the reaction using a pipe in the following order: the hydroformylation reactor 1; the hydrogenation reactor 2; the fore distillation column 3; the second main distillation column 4' and the post distillation column 5.

The hydroformylation reactor 1 will be described in more detail as follows. Any continuous stirred tank reactor or venturi-loop reactor is preferably used as the hydroformylation reactor. Especially, it is preferable that for the hydroformylation reactor, an early reactor should be connected to a following reactor in series; but the reaction temperatures of both reactors should be the same; and the reaction pressure in the early reactor should be higher than that of the following reactor in terms of the efficiency of the reaction. When using the venturi-loop reactor, more preferably, the venture-loop reactor should include a diffusion tube, a distributor plate, and a nozzle having a venture thereby improving the efficiency of the reaction.

The temperature in the reactor is 89° C.; when using two reactors connected in series, it is more preferable that an early pressure is 18 bars and a following pressure 15 bars in terms of the efficiency of the reaction.

The olefin and the synthesis gases are sprayed in the catalyst mixed solution charging inside the reactor by a mean for spraying that is installed on the top part of the reactor.

The mean for spraying is not limited in particular if it can spray the olefin and the synthesis gases in the catalyst mixed solution charging inside the reactor, but for example, an ejector having a nozzle can be used. The nozzle that is installed in the ejector has a role in increasing speed by decreasing a cross-sectional area of spraying of the olefin and the synthesis gases that are supplied inside the reactor due to the high pressure. The diameter of the nozzle may depend to the size of the reactor, and generally it is preferably 1 to 4 mm.

In addition, the ejector preferably combines a venturi tube. The venturi tube includes a inlet part having a linear tube type as known and the diffusion tube having the structure that is becoming wider to its lower part, and the inlet part, through which the olefin and the synthesis gases are flowed, is combined to the ejector and the diameter of the inlet part is the same with the inlet diameter of the diffusion tube and smaller than the outlet diameter of the diffusion tube. At the same time, the outlet direction of the diffusion tube is preferably pointing in the lower part of the reactor.

The diameter of the inlet part is preferably 0.2 to 10 mm, and the length of the divergent inlet is preferably ⅕₀ to ½ of the whole length of the reactor. The diameter of the divergent inlet is the same with that of the inlet part and the diameter of the divergent part outlet is preferably 1.0 to 10 times longer than that of the divergent part inlet. In addition, the length of the divergent part is preferably 0.1 to 10 times longer than that of the inlet part, and the whole length of the venturi tube combined with the inlet part and the divergent part is preferably 0.01 to 0.95 times longer than that of the reactor body and most preferably 0.05 to 0.75 times.

The olefin and the mixture gases that are the raw materials for the reaction are sprayed inside the reactor through the ejector and the venturi tube combined the ejector and then while the olefin and the mixture gas sprayed as mentioned above form the micro-bubbles, they are sprayed in the catalyst mixed solution charging inside the reactor.

The micro-bubbles of the olefin and the mixture gas are contacted to the catalyst mixed solution so that it can provide a sufficient reaction area due to a broad surface area for a gas-liquid contact.

In addition, the flow of the olefin and the mixture gas sprayed by the distributor plate installed between the mean for sprayings and the outlet of the reactor is converted. The retention time of the raw material in the reactor is becoming longer due to the conversion of the flow of the raw material for the reaction thereby improving the efficiency of the reaction. The flow conversion of the raw material for the reaction is determined according to the location and shape of the distributor plate so that the efficiency of the reaction can be controlled.

The distributor plate is preferably located between 1/3 and 2/3 of the length up to the reactor outlet and venturi tube outlet in a direction of the venturi tube from the reactor outlet, and most preferably 1/2. The size of the distributor plate may be 10% to 75% of the inside diameter of the reactor.

As mentioned above, the hydroformylation reaction is proceeded while spraying the olefin and the synthesis gases in the catalyst mixed solution so that there is the reaction mixture containing the aldehyde, the catalyst mixed solution, non-converted olefin, the synthesis gases, other reaction by products, and the like in the reactor. The reaction mixture is collected in the lower part of the reactor by the circulation pipe connected to the outlet of the reactor and the mean for spraying, and then is supplied to the mean for spraying installed on the upper part of the reactor. The reaction mixture is sprayed along with the raw material for the reaction by the circulation and then the raw material is sufficiently mixed with the reaction mixture so that the efficiency of the reaction is improved. The circulation can be controlled by a circulation pump installed to the circulation pipe.

In addition, the circulation pipe may have a heat exchanger and may be not limited to a specific location on the circulation pipe. The reaction mixture separated in any one point of the circulation pipe of the hydroformylation reactor is separated to the catalyst mixed solution and the aldehdye by catalyst/aldehyde separation part (not shown), and then the catalyst mixed solution is circulated to the hydroformylation reactor 1 and the aldehyde is transferred to the hydrogenation reactor 2.

Hereinafter, the catalyst/aldehyde separation part (not shown) will be described in more detail.

The catalyst/aldehyde separation part includes a separation pipe that is separated from any one point of the circulation pipe of the hydroformylation reactor for separating the reaction mixture from the circulation flow; a catalyst/aldehyde separation apparatus that is connected to the separation pipe for separating the catalyst mixed solution and the aldehyde from the reaction mixture; a catalyst mixed solution supply pipe for supplying the catalyst mixed solution to the circulation pipe by connecting to any one point of the catalyst/aldehyde separation apparatus and the circulation pipe; and a aldehyde collection pipe for collecting the aldehyde by connecting to the catalyst/aldehyde separation apparatus.

The reaction mixture of the hydroformylation reactor 1 is separated from any one point of the circulation pipe by the separation pipe of the catalyst/aldehyde separation part and then supplied to the catalyst/aldehyde separation apparatus. The catalyst mixed solution separated from the catalyst/aldehyde separation apparatus is circulated to the hydroformylation reactor through the catalyst mixed solution supply pipe connected to any one point of the circulation pipe. The aldehyde separated from the catalyst/aldehyde separation apparatus is transferred to the hydrogenation reactor through the aldehyde collection pipe connected to the catalyst/aldehyde separation apparatus.

A kind of the catalyst/aldehyde separation apparatus is not limited if it is a mean that is able to separate the catalyst mixed solution the aldehyde from the reaction mixture. For example, the aldehyde that is a low boiling point component among the reaction mixture is discharged in a vapor phase through the heat exchanging process and the catalyst mixed solution that is a high boiling point component may use an evaporation apparatus that can discharge in a liquid phase.

The circulation of the catalyst mixed solution without the aldehyde that is the object may be continuously performed. In some cases, a part of the circulated reaction mixture is discharged to regenerate catalyst or the new catalyst solution or reactivated catalyst solution may be added to the circulation flow of the reaction mixture.

The aldehyde separated from the catalyst/aldehyde separation part is transferred to the hydrogenation reactor 2 and is converted to the aldehyde and alcohol by the hydrogenation reaction.

The hydrogenation reactor 2 includes a mean for spraying for spraying the collected aldehyde and hydrogen gas to the catalyst mixed solution charged inside the reactor; a reactor outlet that is located on the lower part of the reactor for discharging the aldehyde and the hydrogen gas, and the hydrogenation reaction mixture of aldehyde; and a circulation pipe that is connected to the reactor outlet and the mean for spraying for collecting the aldehyde and the hydrogen gas, and the hydrogenation reaction mixture of aldehyde from the reactor outlet and then supplying them to the mean for spraying to circulate them. The hydrogenation reactor may include a loop reactor or a dual fixed-bed reactor. Especially, the reaction condition to the outlet of the hydrogenation reactor is appropriately 110° C. and 25 bars.

The hydrogenation reaction mixture of aldehyde, and the aldehyde and hydrogen gas are sprayed in the catalyst mixed solution charged inside the reactor by the mean for spraying.

The mean for spraying may use the ejector installed with the nozzle. The nozzle that is installed in the ejector has a role in increasing speed by decreasing a cross-sectional area of spraying of the olefin and the synthesis gases that are supplied inside the reactor due to the high pressure.

The diameter of the nozzle may depend to the size of the reactor, and generally it is preferably 1 to 4 mm.

In addition, the ejector preferably combines a venturi tube. The venturi tube includes a inlet part and the diffusion tube, the inlet part is combined to the ejector, and the diameter of the inlet part is the same with the inlet diameter of the diffusion tube, and smaller than the outlet diameter of the diffusion tube. At the same time, the direction of the divergent part 122b outlet is preferably toward the bottom of the reactor. The diameter of the inlet part is preferably 0.2 to 10 mm, the diameter of the divergent inlet is the same with that of the inlet part and the diameter of the divergent outlet is preferably 1.0 to 10 times longer than the diameter of the divergent inlet. The length of the diffusion tube is preferably 0.1 time to 1 time the length of the inlet part, and the length of the whole venturi tube combining the inlet part and the diffusion tube is more preferably 0.01 time to 0.95 time the body length of the reactor.

The hydrogenation reaction mixture of the aldehyde, and the aldehyde and the hydrogen gas are sprayed inside the reactor through the ejector and the venturi tube combined the ejector and then while the aldehyde and the hydrogen gas sprayed as mentioned above form the micro-bubbles, they are sprayed in the catalyst mixed solution charging inside the reactor. The micro-bubbles of the aldehyde and the hydrogen gas are contacted to the catalyst mixed solution so that it can provide a sufficient reaction area due to a broad surface area for a gas-liquid contact. For this reason, the efficiency of the hydrogenation reaction of the aldehyde is improved.

The aldehyde and the hydrogen gas that are sprayed inside the reactor are reacted under presence of the catalyst mixed solution to produce the aldedyde and the alcohol that are the reaction products. For this reason, there are the aldehyde, the alcohol, the hydrogen, the reaction by-product, and the catalyst mixed solution in the reactor. The hydrogenation reaction mixture is collected in the lower part of the reactor and then supplied to the mean for spraying at the upper part of the reactor by the circulation pipe connected to the outlet of the reactor and the mean for spraying. While the hydrogenation reaction mixture is sprayed along with the raw material of the reaction according to the above circulation, the hydrogenation reaction mixture is sufficiently mixed with the raw material thereby improving the efficiency of the reaction. The circulation can be controlled by the circulation pump installed in the circulation pipe.

In addition, the circulation pipe may include the heat exchanger and the location of the heat exchanger is not limited to a specific location on the circulation pipe. The heat exchanger has a role in maintaining the hydrogenation reaction mixture circulated to the reactor to have a suitable temperature for the hydrogenation reaction.

The catalyst mixed solution charged in the reactor is a field containing nickel or copper, and will be described later.

In addition, the hydrogenation reaction mixture that is separated from any one point of the circulation pipe is separated to the catalyst mixed solution, the aldehyde, and the alcohol in the catalyst mixed solution, the aldehyde, and the alcohol separation apparatus; the separated catalyst mixed solution is circulated to the hydrogenation reactor through the catalyst mixed solution supply pipe connected to any one point of the circulation pipe; and then the hydrogenation reaction mixture may be transferred to the distillation apparatus part containing the aldehyde and the alcohol.

Alternatively, the hydrogenation reactor 2 may include the mean for spraying for spraying the aldehyde and the hydrogen gas collected inside the reactor; a nickel catalyst layer having high activity that is located to the point entering the aldehyde and the hydrogen; and the outlet of the reactor that is located at a point passing the copper catalyst layer for discharging the hydrogenation reaction mixture.

The aldehyde and the hydrogen gas are sprayed inside the reactor by the mean for spraying. The aldehyde and hydrogen sprayed are passed the nickel catalyst layer having a high activity and the copper catalyst layer having a low activity in order, and while passing them, the hydrogen is added to the aldehyde to produce the aldehyde and the alcohol.

Generally, the hydrogenation reaction of the aldehyde uses single catalyst of nickel or copper, but the present invention uses two-layer catalyst of nickel and copper. Generally, when using only nickel catalyst having a high activity, the temperature is increased due to an exothermic reaction thereby increasing the temperature to the outlet of the reactor so that a side reaction will be generated. There is a disadvantage such that the side reaction is generated rather than the increase of the efficiency of the reaction due to the catalyst having a high activity. Therefore, the present invention uses the nickel catalyst having a high activity to the inlet of the reactor that has a high concentration of the reactant to be converted so that the reaction speed is increased; and uses the copper catalyst layer having a low activity to the outlet of the reactor that has a low concentration of the reactant to be converted so that the side reaction is suppressed.

The aldehyde and the hydrogen gas sprayed inside the reactor produce the aldehyde and the alcohol that are the reaction product while passing through the two-layer catalyst layer. The hydrogenation reaction product containing the aldehyde and the alcohol passed through the hydrogenation reactor 2 is fractionally distilled.

The fractional distillation is performed at the distillation apparatus part including the fore distillation column; the second main distillation column; and the post distillation column. The distillation apparatus part is a distillation tower or distillation column type, and preferably a type used in the art, generally.

The inlet part and each outlet of the distillation apparatus part are divided, and the division wall is designed to insulate so that the temperature and the pressure in the inlet part and each outlet can be controlled, separately. The hydrogenation reaction product passed through the hydrogenation reactor includes the aldehyde, the alcohol, the hydrogen, the reaction by-product, and the like, and each material is fractionally distilled according the boiling point.

The inlet part is preferably operated at the temperature of 20 to 1° C. and the pressure of 1.0 to 5.0 bars. The conditions for distillation of the hydrogenation reaction product in the inlet part are not limited, especially, and may be set to obtain the desired results considering a volatility of the product, a heat stability of the products, a volatility of the catalyst component, and a heat stability of the catalyst component. However, the conditions are generally selected such that the temperature is in the range of 50 to 200° C. and the pressure is in the range of 1.00 mmHg to 1 MPa.

As shown a flow chart of FIG. 2, FIG. 1(a) of the present invention provides the method for co-production of iso-type reaction product and alcohol from olefin, comprising hydroformylating for obtaining the aldehyde by reacting the micro-bubbles and the catalyst mixed solution while converting the spraying flow of the olefin and the synthesis gases after the micro-bubbles of the olefin and the synthesis gases by spraying the olefin and the synthesis gases ($CO/H_2$) in the catalyst mixed solution using the second main distillation column 4' among the above mentioned apparatus; discharging iso-type alcohol from the second main distillation column through the fore distillation column using the hydrogenation reaction product obtained by adding hydrogen to the normal-aldehyde and iso-aldehyde that are the product obtained from the hydroformylation reaction; and discharging the normal-type alcohol from the post distillation column.

Meanwhile, the hydroformylation is to obtain the aldehyde by reacting the micro-bubbles and the catalyst mixed solution while converting the spraying flow of the olefin and the synthesis gases after forming the micro-bubbles of the olefin and the synthesis gases by spraying the olefin and the synthesis gases ($CO/H_2$) inside the catalyst mixed solution.

While the olefin and the synthesis gases are sprayed, the micro-bubbles are formed and contacted to the catalyst mixed solution so that the sufficient reaction area can be provided due to the broad surface area of the gas-liquid contact. In addition, the reaction is performed while converting the spraying flow of the olefin and the synthesis gases so that the retention time of the raw materials for the reaction in the reactor is becoming longer and then the efficiency of the reaction can be improved.

The hydroformylation is preferably performed using the hydroformylation apparatus part 1 as mentioned above.

The catalyst mixed solution in the hydroformylation reaction is generally used for the hydroformylation reaction, and may include a transition metal catalyst and ligand.

The transition metal catalyst can be used without limitation if it can be generally used in the art, and for example, catalyst having a transition metal as a central metal, such as cobalt (Co), rhodium (Rh), iridium (Ir), ruthenium (Ru), osmium (Os), platinum (Pt), palladium (Pd), iron (Fe), nickel (Ni), and the like, can be used. Specifically, more than one complex catalyst selected from the group consisting of cobaltcarbonyl

[Co$_2$(CO)$_8$], acetylaceton atodicarbonylrhodium [Rh(AcAc)(CO)$_2$], acetylacetonatocarbonylphenylphosphinerhodium [Rh(AcAc)(CO)(TPP)], hydridocarbonyltri(triphenylphosphine)-rhodium [HRh(CO)(TPP)$_3$], acetylacetonatodicarbonyliridium [Ir(AcAc)(CO)$_2$] and hydridocarbonyltri(triphenylphosphine)-iridium[HIr(CO)(TPP)$_3$] can be used.

In addition, three-substituted phosphine, phosphine oxide, amine, amide, iso-nitrile, and the like can be used as ligand, and the three-substituted phosphine can be preferably used. The three-substituted phosphine includes triaryl phosphine, triarylphosphate, alkylarylphosphine, and the like, but is not limited thereto. More specifically, triphenylphosphine, tri-tolylphosphine, triphenylphosphate, n-butylphenylphosphine, and the like can be used.

A solvent used for the catalyst mixed solution may include for example, aldehydes, such as propane aldehyde, butyl aldehyde, pentyl aldehyde, valer aldehyde, and the like; ketones, such as acetone, methyl ethyl ketone, methyl isobutyl ketone, ace-tophenone, cyclohexanone, and the like; alcohols, such as ethanol, pentanol, octanol, thenol, and the like; aromatic type, such as benzene, toluene, xylene, and the like; ethers, such as tetrahydrofuran, dimethoxyethane, dioxane, and the like; and paraffin hydrocarbons, such as heptane, and the like; but is not limited thereto. Propane aldehyde, butyl aldehyde, pentyl aldehyde, valer aldehyde, and the like that are the reaction products can be preferably used.

In addition, for the concentration of the catalyst mixed solution, the weight of the relevant solvent preferably is 30% to 99% ratio of total solution weight.

The olefin that can be used for the present invention includes the olefin having 2 to 20 carbon atoms, but is not limited thereto; more specifically, ethylene, propylene, 1-butene, 1-pentene, 1-hexene, 1-heptene, 1-octene, 1-nonene, 1-decene, 1-undencene, 1-tridecene, 1-tetradecene, 1-pentadecene, 1-hexadecene, 1-heptadecene, 1-octadecene, 1-nonadecene, 1-eicocene, 2-butene, 2-methylpropene, 2-pentene, 2-methylbutene, 2-hexene, 2-heptene, 2-ethylhexene, 2-octene, styrene, 3-phenyl-1-propene, 4-isopropylstyrene, and the like. Ethylene, propylene, 1-butene, 2-butene, 1-pentene, 2-pentene, 2-methylbutene, and the like are more preferably used as the olefin that can be used for the present invention.

The synthesis gases that is another starting material for the hydroformylation reaction is the mixture gas of carbon monoxide and hydrogen, and the mix ratio of CO:H2 is preferably 5:95 to 70:30, more preferably 40:60 to 60:40, and most preferably 45:55 to 55:45, but is not limited thereto.

The mole ratio of the olefin and the synthesis gases is preferably 95:5 to 5:95, and more preferably 75:25 to 25:75.

In addition, the olefin and the synthesis gases are preferably sprayed in the pressure of 5 to 200 bars, respectively. In addition, the linear velocity for spraying the olefin and the synthesis gases is preferably 1 msec to 50 msec, and more preferably 5 msec to 30 msec. The pressure difference between before and after passing the catalyst mixed solution through the mean for spraying 120 is preferably 0.1 bar to 10 bars, and more preferably 0.5 bar to 5 bars.

The reaction is preferably performed at the temperature of 50 to 200° C. and more preferably 50 to 150° C. In addition, the reaction is preferably at the pressure of 5 bars to 100 bars, and more preferably 5 bars to 20 bars.

In addition, preferably the step for hydroformylating further includes the step for circulating the reaction mixture after collecting the reaction mixture to supply the olefin and the synthesis gases altogether in the catalyst mixed solution.

The reaction mixture discharged through the outlet of the reactor 1 is collected, and the reaction mixture is sufficiently mixed with the raw material by the circulation system (shown in FIG. 1(*a*)) supplied inside the reactor 1 so that the efficiency of the reaction is improved. The reaction mixture includes the non-converted olefin, the reaction by-product, the catalyst mixed solution, and the like in addition to the aldehyde (normal-butylaldehyde and iso-butylaldehyde) that are the desired objects.

The circulation system can be achieved by the circulation pipes combined to the mean for spraying of the reactor and the outlet of the reactor 1, and the circulation pump combined to the circulation pipe. The flow amount of the circulated reaction mixture is preferably 0.01 to 20 times the volume charged in the reactor per minute.

In addition, the step for hydroformylating may further include the steps for separating the catalyst mixed solution and the aldehyde after separating a part of the circulated reaction mixture, supplying the separated catalyst mixed solution to the circulation flow, and collecting the aldehyde.

Specifically, when the olefin that is the starting material of the hydroformylation reaction is propylene, the reaction mixture includes butyl aldehyde, more specifically normal-bytylaldehyde and iso-butylaldehyde. The reaction mixture is sent to the catalyst/aldehyde separation apparatus to separate into the aldehyde and the catalyst mixture. And then, the catalyst mixture is circulated to the reactor, and when not producing depending on the iso-type aldehyde, the aldehyde component is transferred to the reaction step in the fore distillation column after hydrogenating.

Among the above steps, the hydrogenation step is the step for obtaining the hydrogenation reaction product containing the aldehyde and the alcohol by adding hydrogen to the aldehyde that is the product obtained from the hydroformylation step. A method for hydrogenating the aldehyde can use one that can be generally used in the art, but is preferably performed as follows.

The step for hydrogenating is preferably performed such that the micro-bubbles of the aldehyde and the hydrogen gas are formed by spraying the collected aldehyde and hydrogen gas inside the catalyst mixed solution, and the micro-bubbles and the catalyst mixed solution are reacted.

The catalyst mixed solution preferably includes Raney-Ni or copper powder. The catalyst mixed solution can be used, and the aldehyde or aldehyde and alcohol is preferably used as a proper solvent. Specifically, the olefin that is the starting material for hydroformylating is propylene so that the normal- or iso-butylaldehyde, and the alcohol are preferably used as the solvent when the material that is introduced to the hydrogenation reactor is butylaldehyde. The composite of the relevant solvent is preferably 2% to 99% and more preferably 20% to 90% based on the weight ratio.

In addition, the hydrogenation of the aldehyde is preferably performed by passing the collected aldehyde and hydrogen gas through the catalyst layer consisting dual layers of Ni catalyst layer having a high activity and Cu catalyst layer having a low activity in order.

The hydrogenation of the aldehyde generally uses a single catalyst, such as nickel or copper, but the present invention is characterized such that the catalyst layer consisting dual layers of nickel and copper is used. The dual catalyst layer pass the aldehyde and hydrogen gas in a fluidized bed as a fixed bed.

Generally, when using only nickel catalyst having a high activity, the side reaction is generated due to raise the temperature to the outlet of the reactor because the temperature is increased by the exothermic reaction. There is a problem due to the generation of the side reaction rather than the increase of the efficiency of the reaction by the catalyst having a high activity.

Therefore, the present invention is characterized such that the nickel catalyst layer having a high activity is used to increase the reaction velocity at the initial reaction, in which the concentration of the reactant should be converted is high, but the copper catalyst layer having a low activity is used to suppress the side reaction at the late reaction, in which the concentration of the reactant that should be converted is low.

The aldehyde for hydrogenating is due to the hydroformylation of the olefin, and preferably includes more than one aldehyde group and 1 to 20 carbons, but is not limited thereto. For example, there are formaldehyde, acetaldehyde, propion aldehyde, n-butyl aldehyde, iso-butylaldehyde, n-valeraldehyde, iso-valeraldehyde, n-hexaaldehyde, n-heptaaldehyde, n-octanal, 2-ethylhexanal, 2-ethylhexenal, n-decanal, 2-ethylbutanal, propargylaldehyde, acrolein, glyoxal, crotonaldehyde, furfural, aldol, hexahydrobenzaldehyde, alpha-citronellal, citral, chloral, trimetylacetaldehyde, dietylacetaldehyde, tetrahydrofurfural, phenylaldehyde, cinnamaldehyde, hydrocinnamaldehyde, and the like. Preferably, there is propionaldehyde, n-butylaldehyde, iso-butylaldehyde or n-valeraldehyde and iso-valeraldehyde.

For example, when the hydroformylation reaction is proceeded using propylene, the normal-butylaldehyde and iso-butylaldehyde are produced. From among these, when the direction is to not produce depending on iso-type aldehyde, the hydrogenation and the reaction in the fore distillation column are performed, and when the direction is to produce depending on iso-type alcohol, the isobutylalcohol is discharged through the reaction in the second main distillation column and the normal-butyl alcohol is discharged through the reaction in the post distillation column.

The aldehyde is preferably sprayed in the velocity of 0.1 to 1 msec. While the aldehyde is sprayed in a certain velocity, the hydrogen is sucked into the hydrogenation reactor 2.

For example, in case of when the hydroformylation reaction proceeds by propylene, the normal-butylaldehyde and iso-butylaldehyde are generated. From among these, when the direction is to produce depending on iso-type aldehyde, the iso-butylaldehyde is discharged from the reaction in the first main distillation column, and when the direction is to produce depending on the alcohol increasing carbon atoms, the remained normal-butylaldehyde produces 2-ethylhexanal by the aldol condensation. The octanol (2-ethylhexanol) can be produced by performing the reactions in the hydrogenation and fore distillation column and the reaction in the post distillation column by using the aldehyde increasing carbon atoms.

The mole ratio of the aldehyde and the hydrogen gas is preferably 1:10 to 10:1. Preferably, the reaction temperature is 50 to 2° C. and the reaction pressure is 2 to 1 bar.

And then, the step for separating the structure isomer of alcohol and the aldehyde is performed by fractionally distillation of the hydrogenation reaction product.

The hydrogenation reaction product includes the aldehyde, the hydrogen, the reaction by-product, and the like as well as the aldehyde and alcohol that are the desired objects. A method for separating the aldehyde and alcohol that are the desired objects can use the methods that are generally used in the art, but preferably use the following methods.

The fractional distillation 3 may use the column having the regions divided by the division wall. The division wall is designed to be insulated, and the temperature and pressure in each divided region may be individually different from the operation temperature and pressure of the column that is traditionally used according to the location and structure of the divided region, and may be suitably controlled according to the plan. The hydrogenation reaction product is fractionally distillated according to the boiling point while passing through each divided region.

The normal- and iso-aldehyde, water, alcohol, and the like that are the low boiling point components among the hydrogenation reaction products are evaporated in the divided region controlled by the relative low temperature and pressure, and then discharged into the upper part of the column. In addition, the iso-aldehyde and alcohol, and the normal-aldehyde and alcohol that are the middle boiling point components are not evaporated or liquefied during the evaporation to discharge from the middle boiling point region of the column.

For example, when the hydroformylation reaction is performed by using propylene, the normal-butylaldehyde and iso-butylaldehyde are generated, and the normal-butylalcohol and iso-butylalcohol are finally obtained through the hydrogenation and fore distillation purification steps, the second main distillation purification step, and the post distillation purification step in order. The separation operation can be generally performed by the distillation operation, such as simple distillation, rectification, thin film distillation, vapor distillation, and the like.

The conditions for distillation are not limited, especially, and may be set to obtain the desired results considering a volatility of the product, a heat stability of the products, a volatility of the catalyst component, and a heat stability of the catalyst component. However, the conditions are generally selected such that the temperature is in the range of 50 to 200° C. and the pressure is in the range of 1.00 mmHg to 1 MPa.

It can be determined through the following Examples that the normal-type alcohol and iso-type alcohol are contented with the range of 1:1 to 15:1 that is N/I selection ratio under the catalyst combinations of one of Rh/TPTP (tri-p-tollylphosphine), Rh/TMPP (tri-m-tollylphosphine), Rh/TOTP (tri-o-tollylphosphine), Rh/CHDP (cyclohexyldiphenylphosphine) Rh/TmPP (trimethoxyphenylphosphine), and Rh/TePP (triethoxyphenylphosphine).

In addition, it is also confirmed through the following Examples that the normal-type alcohol and iso-type alcohol are contented with the range of 8:1 to 12:1 that is N/I selection ratio under Rh/TPP (triphenylphosphine) catalyst.

Meanwhile, it is more preferably in terms of the reaction efficiency that a supply velocity $F_{PPY}$(mol/hr) of the olefin to the reaction, a production velocity $F_{IBO}$(mol/hr) of the isobutanol, and a production velocity $F_{NBO}$(mol/hr) of the normal-butanol are contented with the following Equation I to Equation III under the catalyst combinations of any one of Rh/TPTP, Rh/TMTP, Rh/TOTP, Rh/CHDP, Rh/TmPP, and Rh/TePP:

$$2.4 \le F_{PPY}/F_{IBO} \le 19.2 \tag{I}$$

$$1.3 \le F_{PPY}/F_{NBO} \le 2.4 \tag{II}$$

$$1.0 \le F_{NBO}/F_{IBO} \le 15.0 \tag{III}$$

In addition, it is more preferably that the supply velocity $F_{PPY}$(mol/hr) of the olefin to the reaction, the production velocity $F_{IBO}$(mol/hr) of the isobutanol, and the production velocity $F_{NBO}$(mol/hr) of the normal-butanol are contented with the following Equation I' to Equation III' under Rh/TPP catalyst combination:

$$10.8 \le F_{PPY}/F_{IBO} \le 15.6 \tag{I'}$$

$$1.2 \le F_{PPY}/F_{NBO} \le 1.5 \tag{II'}$$

$$8.0 \le F_{NBO}/F_{IBO} \le 12.0 \tag{III'}$$

Meanwhile, other order of the present invention is as follows: the hydroformylation reactor 1; the first main distillation column 4; the hydrogenation reactor 2; the fore distillation column 3; and the post distillation column 5 in order so that the first main distillation column 4 can be used as shown in the accompanying FIG. 1*b*.

Using the above apparatus, as shown in the flow chart of FIG. 2, the present invention provides the method for co-production of iso-type reaction product and alcohol from olefin, comprising:

hydroformylating for obtaining aldehyde by reacting the micro-bubbles and the catalyst mixed solution while converting the spraying flow of the olefin and the synthesis gases after forming the micro-bubbles of the olefin and the synthesis gases by spraying the olefin and the synthesis gases ($CO/H_2$) in the catalyst mixed solution;

discharging the iso-type aldehyde among the hydroformylation reaction products that are the products obtained from the hydroformylation reaction from the first main distillation column; and separating normal-type alcohol from the post column through the fore distillation column by using the hydrogenation reaction product that is the product obtained by adding hydrogen to the normal-component that is the residue of the hydrogenation reaction product.

For example, when the hydroformylation reaction is proceed by using propylene, the normal-butylaldehyde and iso-butylaldehyde are produced, and when the direction is to produce depending on the isoaldehyde, the iso-butyl aldehyde among these is discharged through the reaction in the first main distillation column and the remained normal-butylaldehyde produces the normal-butanol by the hydrogenation and further fractional distillation process.

The process conditions, the reaction apparatus, and used material according to each step are the same as the mentioned above.

Moreover, it is more preferably in terms of the reaction efficiency that the supply velocity $F_{PPY}$(mol/hr) of the olefin to the reaction, the production velocity $F_{IBO}$(mol/hr) of the isobutylaldehyde, and the production velocity $F_{NBO}$(mol/hr) of the normal-butanol are contented with the following Equation IV to Equation VI under the catalyst combinations of any one of Rh/TPTP, Rh/TMTP, Rh/TOTP, Rh/CHDP, Rh/TmPP, and Rh/TePP:

$$2.4 \leq F_{PPY}/F_{IBA} \leq 19.2 \quad \text{(IV)}$$

$$1.3 \leq F_{PPY}/F_{NBO} \leq 2.4 \quad \text{(V)}$$

$$1.0 \leq F_{NBO}/F_{IBA} \leq 15.0 \quad \text{(VI)}$$

Meanwhile, it is more preferably that the supply velocity $F_{PPY}$(mol/hr) of the olefin to the reaction, the production velocity $F_{IBO}$(mol/hr) of the isobutylaldehyde, and the production velocity $F_{NBO}$(mol/hr) of the normal-butanol are contented with the following Equation IV' to Equation VI' under Rh/TPP catalyst combination:

$$10.8 \leq F_{PPY}/F_{IBA} \leq 15.6 \quad \text{(IV')}$$

$$1.2 F_{PPY}/F_{NBO} \leq 1.5 \quad \text{(V')}$$

$$8.0 \leq F_{NBO}/F_{IBA} \leq 12.0 \quad \text{(VI')}$$

Moreover, another order of the present invention is as follows: the hydroformylation reactor 1; the first main distillation column 4; the aldol condensation reactor 6; the hydrogenation reactor 2; the fore distillation column 3; and the post distillation column 5 in order so that the aldol condensation reactor 6 can be further included to the first main distillation column 4 as shown in the accompanying FIG. 1*c*. The reaction conditions for the aldol condensation reaction are preferably at 1° C. and 2 bars. As the reactor used for the above situation, a continuous stirred-tank reactor (CSTR) charging with NaOH catalyst aqueous solution is effective but is not limited thereto.

Using the above apparatus, as shown in the flow chart of FIG. 2, the present invention provides the method for co-production of iso-type reaction product and alcohol from olefin, comprising: hydroformylating for obtaining aldehyde by reacting the micro-bubbles and the catalyst mixed solution while converting the spraying flow of the olefin and the synthesis gases after forming the micro-bubbles of the olefin and the synthesis gases by spraying the olefin and the synthesis gases ($CO/H_2$) in the catalyst mixed solution; discharging the iso-type aldehyde among the hydroformylation reaction products that are the products obtained from the hydroformylation reaction from the first main distillation column; producing aldehyde increasing carbon atoms by aldol condensation of the normal-component that is the residue of the main distillation column; and separating alcohol component increasing carbon atoms from the post distillation column through the fore distillation column by using the hydrogenation reaction product that is the product obtained by adding hydrogen to the aldehyde increasing carbon atoms that is the product obtained from the aldol condensation step.

As mentioned above, when using the aldol condensation reactor 6 after the first main distillation column 4, the aldehyde and alcohol increasing two times the carbon atoms than that of the aldehyde produced after the hydroformylation reactor can be produced.

For example, when the hydroformylation reaction is proceeded by using propylene, the normal-butylaldehyde and iso-butylaldehyde are produced; when the direction is to produce according to the iso-type aldehyde, the iso-butylaldehyde among these is discharged from the reaction in the first main distillation column, and when the direction is to produce according to the alcohol increasing carbon atoms, the remained normal-butylaldehyde produces 2-ethylhexanal by the aldol condensation. The octanol (2-ethylhexanol) can be produced by performing the reactions in the hydrogenation and fore distillation column and the post distillation column by using the aldehyde increasing carbon atoms.

The process conditions, the reaction apparatus, and the used materials according to each of steps are the same with the mentioned above.

Moreover, it is more preferably in terms of the reaction efficiency that the supply velocity $F_{PPY}$(mol/hr) of the olefin to the reaction, the production velocity $F_{IBO}$(mol/hr) of the isobutylaldehyde, and the production velocity $F_{NBO}$(mol/hr) of the 2-ethylhexanol are contented with the following Equation VII to Equation IX under the catalyst combinations of any one of Rh/TPTP, Rh/TMTP, Rh/TOTP, Rh/CHDP, Rh/TmPP, and Rh/TePP:

$$2.4 \leq F_{PPY}/F_{IBA} \leq 19.2 \quad \text{(VII)}$$

$$2.6 F_{PPY}/F_{EHO} \leq 4.8 \quad \text{(VIII)}$$

$$0.5 \leq F_{EHO}/F_{IBA} 7.5 \quad \text{(IX)}$$

Meanwhile, it is more preferably that the supply velocity $F_{PPY}$ (mol/hr) of the olefin to the reaction, the production velocity $F_{IBO}$(mol/hr) of the isobutylaldehyde, and the production velocity $F_{NBO}$(mol/hr) of the 2-ethylhexanol are contented with the following Equation VII' to Equation IX' under Rh/TPP catalyst combination:

$$10.8 \leq F_{PPY}/F_{IBA} \leq 15.6 \quad \text{(VII')}$$

$$1.4 \leq F_{PPY}/F_{EHO} \leq 2.7 \quad \text{(VIII')}$$

$$4.0 \leq F_{EHO}/F_{IBA} \leq 6.0 \quad \text{(IX')}$$

Advantageous Effects of Invention

A hydroformylation reactor that is contained in an apparatus for coproducing iso-type reaction products and alcohols from olefins according to the present invention provides a sufficient reaction area due to the broad contact surface of olefins and the synthesis gas that are a raw material for reaction by a distributor plate that is installed inside the hydroformylation reactor and a sufficient mixing between the raw materials and the reaction mixture according to the circulation of the reaction mixture so that the efficiency in term of production of aldehydes is excellent. In addition, the hydrogenation reactor for aldehydes suppresses sub-reactions to improve the efficiency in term of production of aldehydes and alcohols.

The apparatus for coproducing iso-type reaction products and alcohols from olefins according to the present invention provides the improved process as mentioned above to save costs for coproducing iso-type reaction products and alcohols from olefins and increase the efficiency in terms of production of alcohols.

The present invention was explained in details around the specific examples in the above sentence, but it can be understood by the person who has general information in the art that various modifications and variations can be possible within the range and the technical spirit of this present invention and those modifications and variations belong to the attached claims.

BRIEF DESCRIPTION OF DRAWINGS

The above and other objects, features and advantages of the present invention will become apparent from the following description of preferred embodiments given in conjunction with the accompanying drawings, in which.

EXPLANATION FOR MARKS ACCORDING TO MAIN PARTS OF FIGURES

Figure 1:
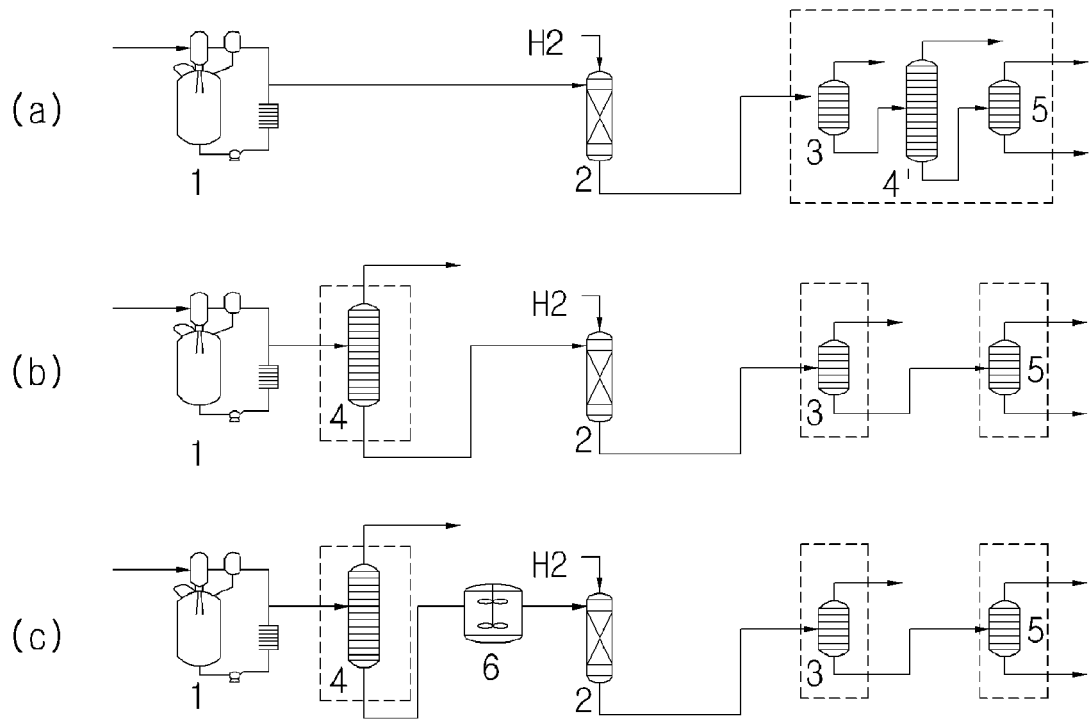
FIG. 1 shows a process chart roughly according to an embodiment of the present invention; (a) is the process for producing iso-type aldehyde and normal-type alcohol from olefin according to Example 1; (b) is the process for producing iso-type aldehyde and normal-type alcohol from olefin according to Example 2; and (c) is the process for producing iso-type aldehyde and normal-type alcohol from olefin according to Example 3.

1: Hydroformylation reactor
2: Hydrogenation reactor
3: Fore distillation column
4: First main distillation column
4': Second main distillation column
5: Post distillation column
6: Aldol condensation reactor

BEST MODE FOR CARRYING OUT THE INVENTION

Hereinafter, the present invention will be described in more detail in light of Examples and Comparative Examples.

The present invention may, however, be embodied in many different forms and should not be construed as being limited to the Examples set forth herein. Rather, these Examples are provided such that this disclosure will be thorough and complete and will fully convey the concept of the present invention to those skilled in the art.

Firstly, each reactor used for the present invention was prepared as follows:

Hydroformylation Reactor 1

Two loop reactors having 30 liters of volume were prepared, and then a nozzle having a diameter of 5 mm, a venturi diffusion tube having a diameter of diffusion tube inlet of 10 mm, a diameter of diffusion tube outlet of 20 mm, and a length of diffusion tube of 30 cm was installed at the head part of each reactor. In addition, the distributor plate having a flat shape of 70 mm diameter was fixed at the point of 200 mm from the lower outlet inside each reactor.

The circulation pump was installed outside the reactor to circulate the reaction solution in a fluid velocity of 20 liter per minute with the spraying nozzle of each reactor head, and the heat exchanger was installed in the outside circulation line in two reactors to remove heat of reaction generated by the reaction. Two reactors were connected in series, and an early reactor (not shown) that is a first reactor among two reactors connected in series connected one among the circulation lines to a top of a following reactor and a controller (not shown) was installed for continuously operating the early reactor at the certain liquid level.

The following reactor 1 that is a second reactor connected to the early reactor in series had the controller for continuously operating at the certain liquid level by transferring the reaction mixture to the evaporation apparatus for separating aldehyde at any one of circulation lines of the reactor like the early reactor. The propylene and synthesis gases that are the raw materials can be supplied separately in each loop reactors connected in series as mentioned above.

By proceeding the reaction, the product from the following reactor 1 was injected to the hydrogenation reactor 2 along with hydrogen gas through the condenser; aldehyde was collected through the evaporation apparatus; remained catalyst solution was circulated to the early and following reactors through a separated pump.

Hydrogenation Reactor 2

A hydrogenation reactor was prepared in a distillation column type having 8 cm diameter and 330 cm length; the nickel catalyst supported in gamma-alumina was filled up to 210 cm from 10 cm of top part; alumina ball was filled to 230 cm therefrom; and the copper catalyst supported in gamma-alumina was filled to 320 cm therefrom to prepare the hydrogenation reactor 2.

The temperature of the reactor 2 outlet was maintained not over 110° C. and the inner pressure was maintained at 25 bar by using the separated circulation pump and outside heat exchanger.

Fore Distillation Column 3 and Post Distillation Column 5

A metal mesh (SUS mesh) and a rashig ring having 1 cm average diameter were used for the fore distillation column 3 and the post distillation column 5; a reboiler was installed at the lowest part of each column and a condenser and a reflux apparatus were installed at the top part.

First Main Distillation Column 4 and Second Main Distillation Column 4'

Two metallic pipes having 8 cm diameter and 148 cm length was prepared.

A metal mesh (SUS mesh) and a rashig ring having 1 cm average diameter were used for the first distillation column 4 and the second distillation column 4'; a reboiler was installed at the lowest part of each column and a condenser and a reflux apparatus were installed at the top part.

Aldol Condensation Reactor 6

A continuous stirred tank reactor (CSTR) having 30 liters was prepared.

Example 1

Preparation of n-BuOH and i-BuOH Applied with Rh/TPTP Catalyst

Step for Producing Catalyst Solution:

30.3 kg of normal-butylaldehyde having 99% purity and 1.6 kg of TPTP (tris-p-tollylphosphine) were injected and then completely dissolved. 45.9 g of acetylacetoneitocarboyltirphenylphosphinerrhodium [Rh(AcAc)(CO)(TPP)] (ROPAC) catalyst that was pre-quantified was further injected to the above mixture to produce 32 kg of catalyst solution.

Step for Hydroformylation Reaction:

16 kg of ROPAC/TPTP catalyst solution that was prepared in advance was charged into two hydroformylation reactors, respectively. After purging with nitrogen gas and propylene two times, respectively, the reaction temperature was maintained at 89° C. through the circulation pump and outside heat exchanger. When the temperature and pressure inside the reactor were stabilized, the propylene was injected until 12 bar pressure inside each reactor.

And then, after stabilizing the temperature and pressure again, propylene that was the raw material was supplied to the early reactor in 3.7 kg/hr flow velocity and the synthesis gases was supplied to the early and following reactors in 2.2 kg and 0.5 kg average flow velocity per hour. The liquid level in each of reactors was maintained at 20 liters; when it is stabilized such that the pressure and the temperature in the early reactor were maintained at 18 bar and 89° C.; and then the pressure and the temperature in the following reactor were maintained at 15 bar and 89° C., while the reaction product was continuously collected in a certain flow velocity, the normal-operation was performed.

Steps for Hydrogenation Reaction and the Reaction in Fore Distillation Column:

Firstly, for hydrogenation reaction and heat exchange, the normal-butanol was used as an initial solvent medium at the initial reaction step, and the circulation flux was maintained at 38 kg per hour.

The reaction product containing the butyl aldehyde produced in the preceding hydrofromylation reaction was supplied to the reactor 2 along with 0.26 kg hydrogen gas per hour. While maintaining the liquid level, the reaction composition was analyzed to reach the operation range of the normal-state.

Then while the reaction product produced from the hydrogenation reaction was constantly supplied to the point of 20 cm from the top part of the fore distillation column 3, the low boiling point components were removed at the top part and the product of the lower part of the column was supplied to the second main distillation column 4' by flowing to produce depending on the iso-type alcohol.

Step for Discharging Product:

The supply to the second main distillation column 4' as mentioned above was constantly supplied to the of 68 cm from the top part of the column, the iso-type alchol was collected from the top part and the product of the lower part of the column was introduced to the point of 25 cm from the top part of the post distillation column 5.

The normal type alcohol was collected from the top part of the post distillation column 5, and the high boiling point component was collected from the lower part of the column.

Type and Content of Collected Product:

After the reactions per each of steps reached to the normal-state as mentioned above, the operation time was total 92 hours; and 1.12 kg of low boiling point component and less than 22 g of iso-butanol were obtained into the top part of the fore distillation column 3 in the reaction. 116.8 kg of isobutanol and 1.6 kg of normal-butanol were totally obtained as the product of the top part of the second main distillation column 4'. In addition, as the product of the top part of the post distillation column 5, 468.6 kg of normal-butanol and less than 1.0 kg of isobutanol were obtained; and as the product of the lower part of the column, 24 kg of heavy component, such as aldehyde trimer and 0.7 kg of normal-butanol were obtained.

It can be confirmed in order to calculate N/I selection ratio that the value added with all of the normal-butanol weights obtained at the top part of the second main distillation column 4', and the top part and the lower part of the post distillation column 5 was divided by the value added with all of isobutanol weights obtained at the top part of the fore distillation column 3, the top part of the second main distillation column 4', and the top part of the post distillation column 5 gives 4.0.

The result for converting energy supplied to the column from the reboiler at the normal-state of operation condition to calory was 2.12 MCal/hr; that is, the fore distillation column 3 was average 0.29 MCal per hour, the second main distillation column 4' was 1.36 MCal, and the post distillation column 5 was 0.47 MCal.

MODE FOR THE INVENTION

Example 2

Production of i-BAL and n-BUOH by using Rh/TPTP Catalyst (1)

Figure 2:
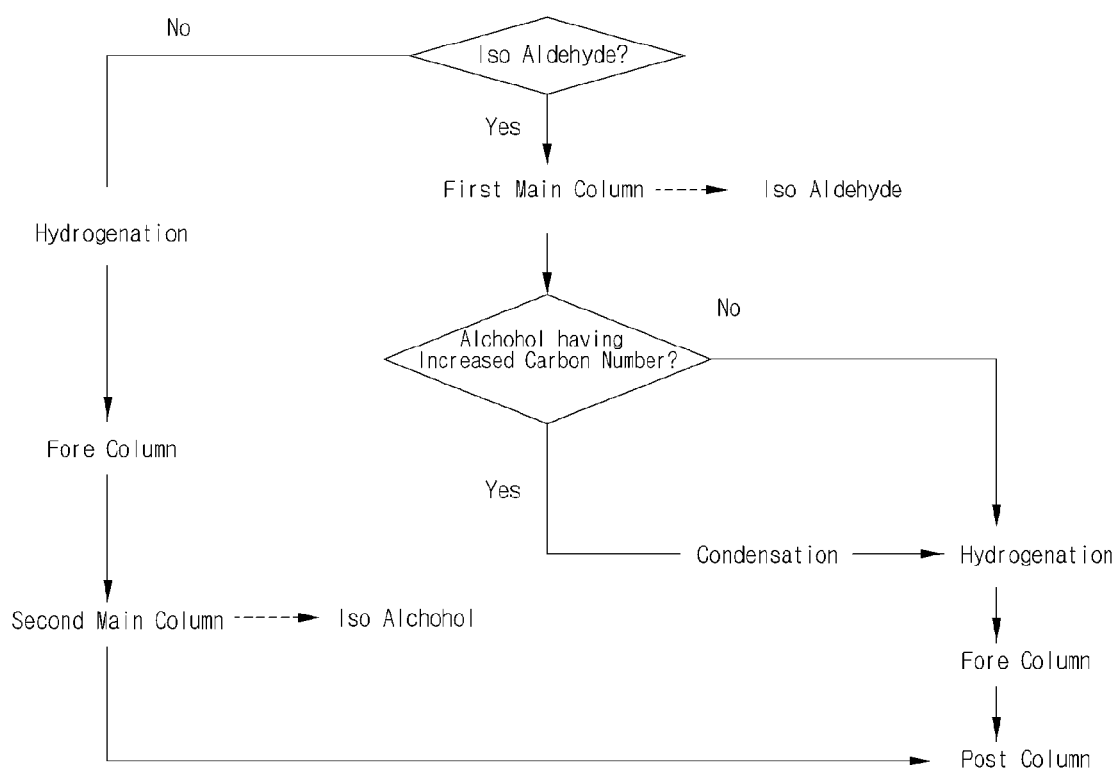
FIG. 2 is a flow chart summarized according to the reaction order of the present invention.

The same process with Example 1 was repeated, but Example 2 used the apparatus as shown in FIG. 1(*b*) and was performed according to the flow chart as shown in FIG. 2.

As a result, 112.5 kg isobutylaldehyde was obtained as the product of the top part of the first main distillation column 4 and 472.1 kg normal-butanol was obtained from the top part of the post distillation column 5.

Example 3

Production of i-BAL and 2-EH by using Rh/TPTP Catalyst (1)

The same process with Example 2 was repeated, but Example 3 used the apparatus as shown in FIG. 1(*c*) and was performed according to the flow chart as shown in FIG. 2.

20 liters solution mixed with 0.95% NaOH catalyst aqueous solution and the product of the lower part containing normal-butyl aldehyde of the main distillation column 4 that was the preceding step in 1:1 ratio was charged into the aldol condensation reactor 6 that was further used in the present Example, and the temperature inside the reactor 6 was maintained at 1° C. and the pressure was maintained 2 bar.

That is, the product of the lower part of the column containing the normal-butyl aldehdye of the first main distillation column 4 was continuously injected to maintain 20 liters of liquid level while the stirring number was maintained at 2 rpm; at the same time, 0.95% NaOH catalyst aqueous solution was injected at the same weight ratio to the reactor 6; and the reaction product from the reactor 6 was injected to the hydrogenation reactor 2 by using the same process with Example 2.

Through the final separation purification step, 483.5 kg of 2-ethylhexylalcohol was obtained and 122.4 kg of isobutylaldehyde was obtained from the top part of the first main distillation column 4.

Example 4

Production of i-BuOH and n-BuOH by using Rh/TPTP Catalyst (2)

The continuous experiment was performed with the same method with Example 1 except injecting 0.8 kg TPTP of Example 1. As a result, 147.2 kg of isobutanol (i-BuOH) and 438.1 kg of normal-butanol (n-BuOH) were obtained. At this time, N/I selection ratio was 3.0.

Example 5

Production of i-BAL and n-BuOH by using Rh/TPTP Catalyst (2)

As a result for continuously operating the same method with Example 2 except producing the catalyst by using the same method with Example 4, 152.3 kg of isobutylaldehyde and 431.6 kg of normal-butanol (n-BuOH) were obtained.

Example 6

Production of i-BAL and 2-EH by using Rh/TPTP Catalyst (2)

As a result for continuously operating the same method with Example 3 except producing the catalyst by using the same method with Example 4, 151.2 kg of isobutylaldehyde and 447.1 kg of 2-ethylhexanol were obtained.

Example 7

Production of i-BuOH and n-BuOH by using Rh/TMTP Catalyst

As a result for continuously operating the same method with Example 1 except dissolving by injecting 2.1 kg TMTP (tri-m-tollylphosphine) having 99% purity instead of TPTP in the step for producing catalyst, 79.8 kg of isobutanol and 490.3 kg of normal-butanol were obtained. N/I selection ratio was 6.1.

Example 8

Production of i-BAL and n-BuOH by using Rh/TMTP Catalyst

As a result for continuously operating the same method with Example 2 and producing the catalyst solution by using the same method with Example 7, 76.9 kg of isobutylaldehyde and 487.1 kg of normal-butanol were obtained.

Example 9

Production of i-BAL and 2-EH by using Rh/TMTP Catalyst

As a result for continuously operating the same method with Example 3 and producing the catalyst solution by using the same method with Example 7, 80.2 kg of isobutylaldehyde and 492.7 kg of 2-ethylhexanol were obtained.

Example 10

Production of i-BuOH and n-BuOH by using Rh/TOTP Catalyst

As a result for continuously operating the same method with Example 1 except dissolving by injecting 3.2 kg TOTP (tri-o-tollylphosphine) having 99% purity instead of TPTP in the step for producing catalyst, 228.1 kg of isobutanol and 342.5 kg of normal-butanol were obtained. N/I selection ratio was 1.5.

Example 11

Production of i-BAL and n-BuOH by using Rh/TOTP Catalyst

As a result for continuously operating the same method with Example 2 and producing the catalyst solution by using the same method with Example 10, 223.1 kg of isobutylaldehyde and 340.9 kg of 2-ethylhexanol were obtained.

Example 12

Production of i-BAL and 2-EH by using Rh/TOTP Catalyst

As a result for continuously operating the same method with Example 3 and producing the catalyst solution by using the same method with Example 10, 235.7 kg of isobutylaldehyde and 346.1 kg of 2-ethylhexanol were obtained.

Example 13

Production of i-BuOH and n-BuOH by using Rh/CHDP Catalyst

As a result for continuously operating the same method with Example 1 except dissolving by injecting 1.06 kg CHDP (cyclohexyldiphenylphosphine) having 99% purity instead of TPTP in the step for producing catalyst, 193.3 kg of isobutanol and 386.8 kg of normal-butanol were obtained. N/I selection ratio was 2.0.

Example 14

Production of i-BAL and n-BuOH by using Rh/CHDP Catalyst

As a result for continuously operating the same method with Example 2 and producing the catalyst solution by using the same method with Example 13, 198.3 kg of isobutylaldehyde and 391.0 kg of normal-butanol were obtained.

Example 15

Production of i-BAL and 2-EH by using Rh/CHDP Catalyst

As a result for continuously operating the same method with Example 3 and producing the catalyst solution by using the same method with Example 13, 196.2 kg of isobutylaldehyde and 389.1 kg of 2-ethylhexanol were obtained.

Example 16

Production of i-BuOH and n-BuOH by using Rh/TmPP Catalyst

As a result for continuously operating the same method with Example 1 except dissolving by injecting 0.8 kg TmPP (trimethoxyphenylphosphine) having 99% purity instead of TPTP in the step for producing catalyst, 169.1 kg of isobutanol and 422.3 kg of normal-butanol were obtained. N/I selection ratio was 2.5.

Example 17

Production of i-BAL and n-BuOH by using Rh/TmPP Catalyst

As a result for continuously operating the same method with Example 2 and producing the catalyst solution by using the same method with Example 16, 174.1 kg of isobutylaldehyde and 418.6 kg of normal-butanol were obtained.

Example 18

Production of i-BAL and 2-EH by using Rh/TmPP Catalyst

As a result for continuously operating the same method with Example 3 and producing the catalyst solution by using the same method with Example 16, 171.9 kg of isobutylaldehyde and 427.3 kg of 2-ethylhexanol were obtained.

Example 19

Production of i-BuOH and n-BuOH by using Rh/TPP Catalyst

As a result for continuously operating the same method with Example 1 except dissolving by injecting 3.2 kg TPP (triphenylphosphine) having 99% purity instead of TPTP in the step for producing catalyst, 52.7 kg of isobutanol and 525.4 kg of normal-butanol were obtained. N/I selection ratio was 10.0.

Example 20

Production of i-BAL and n-BuOH by using Rh/TPP Catalyst

As a result for continuously operating the same method with Example 2 and producing the catalyst solution by using the same method with Example 19, 49.8 kg of isobutylaldehyde and 511.0 kg of normal-butanol were obtained.

Example 21

Production of i-BAL and 2-EH by using Rh/TPP Catalyst

As a result for continuously operating the same method with Example 3 and producing the catalyst solution by using the same method with Example 19, 51.2 kg of isobutylaldehyde and 509.8 kg of 2-ethylhexanol were obtained.

As shown in Examples 1 to 6 used with the Rh/TPTP catalyst combination, Examples 7 to 9 used with Rh/TMTP catalyst combination, Examples 10 to 12 used with Rh/TOTP catalyst combination, Examples 13 to 15 used with Rh/CHDP catalyst combination, Examples 16 to 18 used with Rh/TmPP, and Examples 19 to 21 used with Rh/TPP, it could be confirmed that when using TPP, N/I selection ratio was improved to 10:1, and also when using the catalyst above TPP, N/I selection ratio was improved to 1.5 to 6.1.

The invention claimed is:

1. A method for coproducting iso-type reaction product and alcohol from olefin in an apparatus comprising a hydroformylation reactor, a hydrogenation reactor, a fore distillation column, a second main distillation column, and a post-distillation column, the method, comprising:
    producing normal-aldehyde and iso-aldehyde by reacting synthesis gases ($CO/H_2$) and olefin with a catalyst mixture solution by performing a hydroformylation in the hydroformylation reactor, the hydroformylation comprising:
        generating micro-bubbles of the olefin and the synthesis gases by spraying the olefin and the synthesis gases through a distributor plate of the hydroformylation reactor and into the catalyst mixture solution, the catalyst mixture solution comprising:
        a solvent:
        a transition metal catalyst selected from the croup consisting of rhodium (Rh), cobalt (Co), and iridium; and
        a ligand selected from the group consisting of triphenylphosphine (TPP), tri-p-tollylphosphine (TPTP), tri-m-tollylphosphine (TMTP), tri-o-tollylphosphine (TOTP), cyclohexyldiphenylphosphine (CHDP), trimethoxyphenylphosphine (TmPP), triethoxyphenylphosphine (TePP), trimethylphosphine, triethylphosphine, tri-n-propylphosphine, tri-n-butylphosphine, tri-n-octylphosphine, tri-n-octadecylphosphine, n-octadecyldimethylphosphine, diethyl-n-octylphosphine, and ethylmethyl-n-propylphosphine;
    transferring the normal-aldehyde and the iso-aldehyde to the hydrogenation reactor;
    producing normal-type alcohol and iso-type alcohol from the transferred normal-aldehyde and iso-aldehyde by performing a hydrogenation in the hydrogenation reactor;
    transferring the normal-type alcohol and the iso-type alcohol to the second main distillation column, the second main distillation column comprising the fore distillation column and the post distillation column;
    discharging the iso-type alcohol from the second main distillation column through the fore distillation column; and
    discharging the normal-type alcohol from the second main distillation column through the post distillation column.

2. A method for coproducting iso-type reaction product and alcohol from olefin, in an apparatus comprising a hydroformylation reactor, a hydrogenation reactor, a fore distillation column, and a second main distillation column, the method comprising:
    producing normal-aldehyde and iso-aldehyde by reacting synthesis gases ($CO/H_2$) and olefin with a catalyst mixture solution by performing a hydroformylation in the hydroformylation reactor, the hydroformylation comprising:
        generating micro-bubbles of the olefin and the synthesis gases by spraying the olefin and the synthesis gases through a distributor plate of the hydroformylation reactor and into the catalyst mixture solution, the catalyst mixture solution comprising:
        a solvent;
        a transition metal catalyst selected from the group consisting of rhodium (Rh), cobalt (Co), and iridium (Ir); and a ligand selected from the group consisting triphenylphosphine (TPP), tri-p-tollylphosphine (TPTP), tri-m-tollylphosphine (TMTP), tri-o-tollylphosphine (TOTP), cyclohexyldiphenylphosphine (CHDP), trimethoxyphenylphosphine (TmPP), triethoxyphenylphosphine (TePP), trimethylphosphine, triethylphosphine, tri-n-propylphosphine, tri-n-butylphosphine, tri-n-octylphosphine, tri-n-octadecylphosphine, n-octadecyldimethylphosphine, diethyl-n-octylphosphine, and ethylmethyl-n-propylphosphine;

transferring the normal-aldehyde and the iso aldehyde to the first main distillation column;

discharging the iso-aldehyde from the first main distillation column through an outlet;

transferring the normal-aldehyde from the first main distillation column to the hydrogenation reactor;

producing normal-type alcohol from the normal-aldehyde in the hydrogenation reactor;

transferring the normal-type alcohol to the second main distillation column, the second main distillation column comprising the fore distillation column; and discharging the normal-type alcohol from the post distillation column through the fore distillation column.

3. A method for coproducting iso-type reaction product and alcohol from olefin in an apparatus comprising a hydroformylation reactor, a hydrogenation reactor, an aldol condensation reactor, a fore distillation column, a second main distillation column, and a post-distillation column, the method, comprising:

producing normal-aldehyde and iso-aldehyde by reacting synthesis gases ($CO/H_2$) and olefin with a catalyst mixture solution by performing a hydroformylation in the hydroformylation reactor, the hydroformylation comprising:

generating micro-bubbles of the olefin and the synthesis gases by spraying the olefin and the synthesis gases into the catalyst mixture solution, the catalyst mixture solution comprising:

a solvent:

a transition metal catalyst selected from the group consisting of rhodium (Rh), cobalt (Co), and iridium (Ir); and a ligand selected from the group consisting triphenylphosphine (TPP), tri-p-tollylphosphine (TPTP), tri-m-tollylphosphine (TMTP), tri-o-tollylphosphine (TOTP), cyclohexyldiphenylphosphine (CHDP), trimethoxyphenylphosphine (TmPP), triethoxyphenylphosphine (TePP), trimethylphosphine, triethylphosphine, tri-n-propylphosphine, tri-n-butylphosphine, tri-n-octylphosphine, tri-n-octadecylphosphine, n-octadecyldimethylphosphine, diethyl-n-octylphosphine, and ethylmethyl-n-propylphosphine;

transferring the normal-aldehyde and the iso-aldehyde to the first main distillation column;

discharging the iso-aldehyde from the first main distillation column through an outlet;

transferring the normal-aldehyde from the first main distillation column to an aldol condensation reactor;

producing normal-aldehyde having an increased carbon number by performing an aldol condensation in the aldol condensation reactor;

transferring the normal-aldehyde having an increased carbon number from the aldol condensation reactor to a hydrogenation reactor;

producing normal-type alcohol from the normal-aldehyde having an increased carbon number in the hydrogenation reactor;

transferring the normal-type alcohol to a second main distillation column, the second main distillation column comprising a fore distillation column; and discharging the normal-type alcohol having an increased carbon number, from the second main distillation column through the fore distillation column.

4. The method for coproducting iso-type reaction product and alcohol from olefin according to any one of claim 1 to claim 2, wherein the hydroformylation reactor is a continuous stirred tank reactor or a venturi-loop reactor having a spraying means at the top of the reactor, a reactor outlet, and a distributor plate installed between the spraying means and the reactor outlet, wherein the distributor plate is located between ⅓ to ⅔ of the length from the end of the spraying means to the reactor outlet; and wherein the hydrogenation reactor is a loop reactor or a dual fixed reactor having a spraying means, and wherein a nickel catalyst layer is positioned at an entrance point of the hydrogenation reactor and a copper catalyst layer is positioned at an outlet of the hydrogenation reactor.

5. The method for coproducting iso-type reaction product and alcohol from olefin according to any one of claim 1 to claim 3, wherein the olefin is selected from the group consisting of ethylene, propylene, 1-butene, 1-hexene, 1-octene, 1-nonene, 1-decene, 1-undencene, 1-tridecene, 1-tetradecene, 1-pentadecene, 1-hexadecene, 1-heptadecene, 1-octadecene, 1-nonadecene, 1-eicocene, 2-butene, 2-methylpropene, 2-pentene, 2-hexene, 2-heptene, 2-ethylhexene, 2-octene, styrene, 3-phenyl-1-propene, and 4-isopropylstyrene.

6. The method for coproducting iso-type reaction product and alcohol from olefin according to claim 4, wherein the N/I selectivity ratio of the normal alcohol and iso alcohol by using the catalyst combination of one of Rh/TPTP, Rh/TMTP, Rh/TOTP, Rh/CHDP, Rh/TmPP, and Rh/TePP is in the range of 1:1 to 15:1.

7. The method for coproducting iso-type reaction product and alcohol from olefin according to claim 4, wherein the N/I selectivity ratio of the normal alcohol and iso alcohol by using Rh/TPP catalyst is in the range of 8:1 to 12:1.

8. The method for coproducting iso-type reaction product and alcohol from olefin according to claim 3, wherein the hydroformylation reactor is a continuous stirred tank reactor or a venturi-loop reactor having a spraying means at the top of the reactor, a reactor outlet, and a distributor plate installed between the spraying means and the reactor outlet, wherein the distributor plate is located between ⅓ to ⅔ of the length from the end of the spraying means to the reactor outlet;

wherein the hydrogenation reactor is a loop reactor or a dual fixed reactor having a spraying means, and wherein a nickel catalyst layer is positioned at an entrance point of the hydrogenation reactor and a copper catalyst layer is positioned at an outlet of the hydrogenation reactor; and wherein the aldol condensation reactor is a continuous stirred-tank reactor charged with a NaOH catalyst aqueous solution.

\* \* \* \* \*